US006426404B1

(12) United States Patent
Podolsky

(10) Patent No.: US 6,426,404 B1
(45) Date of Patent: Jul. 30, 2002

(54) RECEPTOR FOR INTESTINAL TREFOIL FACTOR

(75) Inventor: Daniel K. Podolsky, Wellesley Hills, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 09/140,140

(22) Filed: Aug. 25, 1998

Related U.S. Application Data

(60) Provisional application No. 60/056,787, filed on Aug. 25, 1997.

(51) Int. Cl.⁷ ..................... C07K 14/425; G01N 27/26; C12N 15/00; C12N 15/85
(52) U.S. Cl. .................. 530/350; 530/300; 530/412; 530/402; 435/69.1; 435/70.1; 435/325; 204/182.8
(58) Field of Search .................. 530/350, 300, 530/412, 402; 435/69.1, 70.1, 325; 204/182.8

(56) References Cited

U.S. PATENT DOCUMENTS 5,783,416 A 7/1998 Thim et al. ............. 435/69.1

FOREIGN PATENT DOCUMENTS

WO WO 96/06861 3/1996

OTHER PUBLICATIONS

Burgess et al., J. Cell Biol. 111:2129–38 (1990).
Lazar et al., Mol. Cell. Biology 8(3):1247–52 (1988).
Parsons, J.A. (editor), "Peptide Hormones," published by University Park Press, see Chapter 1, pp. 1–7 by Rudinger (1976).
Maniatis, T., et al. 1982, Molecular Cloning, A Laboratory Manual, Cold Spring Harbor Laboratory, Cold Spring Harbor, New York, pp. 224–246, 270–307, 310–352, 404–433.
Jorgensen, K.D., et al., 1982, Pancreatic Spasmolytic Polypeptide (PSP): III. Pharmacology of a new porcine pancreatic polypeptide with spasmolytic and gastric acid secretion inhibitory effects, Reg. Pep. 3:231–243.
Thim, L., et al., 1982, Pancreatic Spasmolytic Polypeptide (PSP): II. Radioimmunological determination of PSP in porcine tissue, plasma and pancreatic juice, Regulatory Peptides, 3:221–230.
Jorgensen, K.H., et al., 1982, Pancreatic Spasmolytic Polypeptide (PSP): I. Preparation and initial chemical characterization of a new polypeptide from porcine pancreas, Regulatory Peptides, 3:207–219.
Jakowlew, S.B., et al., 1984, Sequence of the pS2 mRNA induced by estrogen in the human breast cancer cell line MCF–7, 12:2861–2878.
Frandsen, E.K., et al., 1986, Receptor binding of pancreatic spasmolytic polypeptide (PSP) in rat intestinal mucosal cell membranes inhibits the adenylate cyclase activity, Regulatory Peptides, 16:291–297.
Rio, M.C., et al., 1988, Breast Cancer–Associated pS2 Protein: Synthesis and Secretion by Normal Stomach Mucosa, Science, 241:705–708.
Podolsky, D.K., et al., 1988, Latent Transformed Growth–inhibiting Factor in Human Malignant Effusions, Cancer Research, 48:418–424.
International Search Report for PCT/US92/01200 dated May 11, 1992.
Hauser et al., "hP1.8, a human P–domain peptide homologous with rat intestinal trefoil factor . . . ," Proceeedings of the National Academy of Science 90:6961–6965, 1993.
Sands et al., "The Trefoil Peptide Family," Annual Review of Physiology 58:253–273. 1996.
Chinery et al., "Expression and purification of a trefoil peptide motif in a B–galactosidase fusion . . . " Europ. J. Biochem. 212:557–563, 1993.
Chinery et al., "Immunoprecipitation and Characterization of a Binding Protein Specific for the Peptide . . . " Peptides 16(4):749–755, 1995.
Tan et al., "Characterization of a Putative Receptor for Intestinal Trefoil Factor in Rat . . . " Biochem. & Biophys. Res. Comm. 237:673–677, 1997.

Primary Examiner—Yvonne Eyler
Assistant Examiner—Nirmal S. Basi
(74) Attorney, Agent, or Firm—Clark & Elbing LLP

(57) ABSTRACT

A substantially pure intestinal trefoil factor receptor which is obtainable from intestinal cells and has a molecular weight of about 50 to 60 kD or about 75 to 80 kD.

2 Claims, 1 Drawing Sheet

RECEPTOR FOR INTESTINAL TREFOIL FACTOR

CROSS REFERENCE TO RELATED APPLICATIONS

This application claims priority from U.S. Provisional Application Ser. No. 60/056,787, filed Aug. 25, 1997.

BACKGROUND OF THE INVENTION

ITF is abundantly expressed by specialized mucus-producing cells of the gastrointestinal tract and is secreted onto the mucosal surface, where it appears to act extracellularly on epithelial cells through undefined mechanisms.

ITF plays an important role in restitution, a rapid process during which epithelial cells spread and migrate across the basement membrane to cover shallow defects of the mucosal surfaces of the gastrointestinal tract. Colonic restitution is absent in mice made ITF deficient by homologous recombination; the otherwise trivial colonic injury induced by 2.5% dextran sodium sulfate is lethal in these animals. Moreover, ITF has been shown to prevent acute gastrointestinal injury caused by alcohol or indomethacin and to rapidly reseal erosions caused by these agents.

SUMMARY OF THE INVENTION

The invention is based on the discovery of ITF receptor (ITFR). ITFR can be purified and/or isolated from intestinal cells using an ITF fusion protein, e.g., ITF-thioredoxin. An ITF fusion protein such as ITF-thioredoxin is capable of binding to ITFR expressed on intestinal cells. The specificity of such binding activity can be confirmed by adding excess of ITF which competes with the ITF fusion protein such as ITF-thioredoxin for binding to ITFR. Subsequently, the ITF fusion protein/ITFR complex can be purified using an affinity column, e.g., a thioredoxin affinity resin. The ITFR present in the ITF fusion protein/ITFR complex can be isolated using routine protein purification methods.

The present invention features a substantially pure intestinal trefoil factor receptor (ITFR), characterized in that it specifically binds to human ITF, has a molecular weight of about 50 to 60 kD or about 75 to 80 kD, and is expressed by intestinal or colonic cells.

Also within the invention is a preparation of antibodies which specifically bind to ITFR and do not specifically bind to other proteins.

Another aspect of the invention provides a method of obtaining a substantially pure intestinal trefoil factor receptor (ITFR) which comprises incubating intestinal trefoil factor-thioredoxin (ITF-thioredoxin) with an intestinal or colonic cell lysate in the presence and absence of ITF, obtaining an ITF-thioredoxin complex, wherein the complex binds to a thioredoxin affinity resin, and isolating the substantially pure ITFR from the ITF-thioredoxin complex, wherein the polypeptide is associated with the ITF-thioredoxin complex in the absence of ITF, but not in the presence of ITF.

As used herein, the term "substantially pure polypeptide" is meant a ITFR polypeptide which has been separated from components which naturally accompany it. Typically, the polypeptide is substantially pure when it is at least 60%, by weight, free from the proteins and naturally-occurring organic molecules with which it is naturally associated. Preferably, the preparation is at least 75%, more preferably at least 90%, and most preferably at least 99%, by weight, of ITFR polypeptide.

A substantially pure ITFR polypeptide may be obtained, for example, by extraction from a natural source (e.g., intestinal epithelial cells), by expression of a recombinant nucleic acid encoding a ITFR polypeptide, or by chemically synthesizing the protein. Purity can be measured by any appropriate method, e.g., those described in column chromatography, polyacrylamide gel electrophoresis, or by HPLC analysis.

A protein is substantially free of naturally associated components when it is separated from those contaminants which accompany it in its natural state. Thus, a protein which is chemically synthesized or produced in a cellular system different from the cell from which it naturally originates will be substantially free from its naturally associated components. Accordingly, substantially pure polypeptides include those derived from eukaryotic organisms but synthesized in *E. coli* or other prokaryotes.

The present invention provides substantially pure ITFR, e.g., human ITFR, and enables molecular characterization and modification of ITFR. For example, the substantially pure ITFR of the present invention can be used to generate anti-ITFR antibodies and to isolate gene(s) encoding ITFR. The cDNA encoding ITFR can be used to make recombinant ITFR, mutants of ITFR, and fragments of ITFR. Human ITFR can be used to develop treatments for gastrointestinal disease conditions associated with the activities of ITF.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION OF THE INVENTION

Figure 1:
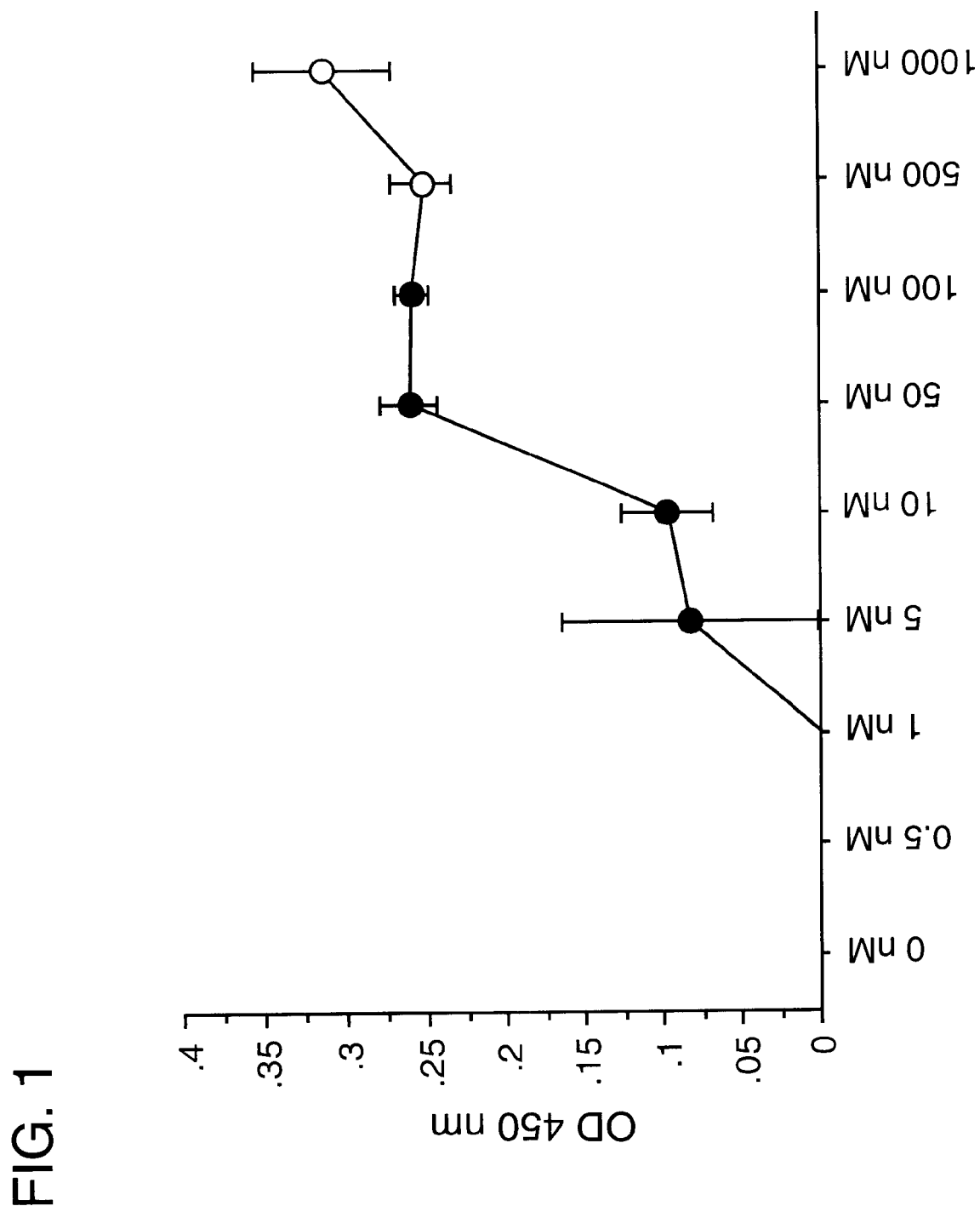
FIG. 1 is a graph depicting the result of an ITF ELISA assay. In this assay specific binding of an ITF fusion protein, ITF-TRX, to ITFR on the surface of a rat non-transformed intestinal epithelial cell line IEC-6 was measured.

Intestinal trefoil protein receptor (ITFR) is a novel receptor protein that binds intestinal trefoil factor (ITF), a protein expressed in the digestive system that is useful for treatment of various digestive disorders (e.g., peptic ulcer and inflammatory bowel diseases) and injuries (e.g., injury caused by bacterial infection or radiation). ITF, the gene encoding ITF, and methods for using ITF are described at length in co-pending U.S. patent application U.S. Ser. No. 08/631, 649, filed Apr. 12, 1996, hereby incorporated by reference.
Identification and Characterization of Intestinal Trefoil Protein Receptor Any cells having ITF and/or ITFR activity can be candidates to be employed in ITFR binding and purification assays. Suitable cells include intestinal and colonic cells, preferably intestinal and colonic epithelial cells. Gastric cell lines or mucosa can also be used. Either primary isolated cells or mucosa, or established cell lines from these sites can be used. For example, rat nontransformed intestinal epithelial cell line IEC-6, human colon cancer derived cell lines HT-29, CaCo2, and LS174 (ATCC; 10801 University Boulevard, Manassas, Va., 20110-2209), and human gastric cancer derived cell lines AGS and KATO-III all can be used for ITFR purification.

Cells having ITFR and/or ITF activity can be identified based on the specific binding between ITF and ITFR expressed on the cell surface using any applicable means available in the art, e.g., an ELISA assay. The binding between an ITF fusion protein and ITFR can be detected via an anti-ITF antibody or an antibody which specifically binds the polypeptide fragment fused with ITF, e.g., an anti-thioredoxin antibody.

To identify ITFR, an ITF fusion protein can be used to probe for proteins specifically interacting with ITF in various binding assays. An ITF fusion protein including all or a portion of ITF can be used to bind ITFR. Preferably an ITF fusion protein contains just the mature peptide without the signal region of ITF. See FIG. 1 in Sands et al., *Annu. Rev. Physiol.* vol. 58: 253–73, 1996.

The ITF fusion protein also includes a separate purification or binding entity to facilitate identification and isolation of the fusion protein. Such an entity can be any applicable compound, e.g., a polypeptide or other entity which can be fused to ITF, but does not substantially interfere with binding of ITF to ITFR. Suitable compounds include but are not limited to thioredoxin, GST tag, FLAG tag, GFP tag, poly-Histidine tag, and c-myc tag.

The cells used in ITFR purification assay can be lysed by any suitable means which maintains the structural integrity of ITFR, especially the ITF binding domain of ITFR. The cell lysate can be incubated with a suitable ITF fusion protein as discussed above in conditions optimal for a protein binding reaction. Excess ITF can be added to the binding reaction as a control for binding specificity. The ITFR binding complex, e.g., ITFR/ITF-TRX binding complex can be isolated and/or purified by means suitable for isolation of the binding entity or tag. Western blot or any other suitable techniques can be used to detect the protein factors forming the ITF-ITFR binding complex.

ITFR-bearing cells were identified as follows. Both human (LS174) and rat (IEC-6) intestinal epithelial cells were grown separately to confluence in 96 well plates, washed three times with PBS containing 0.1% BSA for 20 minutes at 37° C., and then washed with cold 0.1% BSA and PBS. Thereafter, recombinant human ITF-TXR (prepared as above) with or without ITF was added to the cells and the cells were incubated at 4° for 60 minutes.

Next, the cells were washed three times and the first antibody,. anti-thioredoxin (1 to 1000 dilution), was added in PBS containing 0.1% BSA. After 60 minutes at room temperature, the cells were washed three times and the second antibody, anti-mouse IgG (1 to 10,000 dilution), was added. Anti-thioredoxin antibody was detected using a ELISA assay (Vectastain, Burlingame, Calif.). FIG. 1 illustrates the results of a typical such assay employing ITF-TRX and IEC-6 cells.ITF-TRX was prepared as follows. A cDNA encoding the portion of human ITF corresponding to the 59 amino acid mature peptide and lacking the signal sequence (FIG. 1, Sands et al., *Annu. Rev. Physiol.* 58:253–73, 1996.) was generated by RT-PCR from human colon MRNA using primers which created KpnI and SalI restriction sites. The resulting cDNA was digested with KpnI and SalI and ligated into pTRXFUS thioredoxin fusion protein vector (Invitrogen, San Diego, Calif.). ITF-TRX protein was then expressed in *E. coli* according to the manufacturer's protocol (Invitrogen). Recombinant ITF-TRX fusion protein was purified using thioredoxin affinity resin column (Invitrogen) and Superose 12 gel filtration chromatography. This yielded apparently homogenous ITF-TRX as assessed by SDS-PAGE and Western blotting.

ITFR containing cell lysates were prepared as follows. Both IEC-6 cells and LS174 cells were grown separately in 10 cm plates using PBS. After washing cell monolayers three times, the cells were incubated overnight with 0.1% FBS in DMEM medium by standard techniques. The cells were washed three times and then lysed by adding 1 ml/10 cm dish of lysis buffer (0.5% NP-40 PBS (pH 7.4), 1 mM EDTA, 57 nM PMSF, 5 mg/ml Aprotinin, 1 mg/1 ml Leupepsin, 2 mM Na-vandaium, 100 nM NaF, and 10 mM pyrophosphotetrasodium) and incubating on ice for 30 minutes. The cell material was harvested by cell scraper and centrifuged at 15,000 rpm for 15 minutes.

The cell lysates from IEC-6 and LS174 cells were incubated (400 $\mu$g protein per tube) with ITF-TRX fusion protein (200 nM) in the presence or absence of excess ITF. After overnight incubation DSS (dextran sodium sulphate) was added to a final concentration of 1 nM. The reaction mixture was incubated at 4° C. for two hours. The reaction was stopped by ice-cold 1 M Tris (pH 7.4; final concentration 50 nM), incubated for 15 minutes at 4° C., and then centrifuged for 15 minutes at 15,000 rpm. The supernatant was added to 50 $\mu$L of thioredoxin affinity resin and mixed gently at 4° for 2 to 3 hours on a rotating platform. The affinity resin was washed three times in 1 mM $\beta$-mercaptoethanol and 50 mM Tris buffer and then washed twice with 5 mM $\beta$-mercaptoethanol in 50 mM Tris buffer. Next, the resin material was boiled for 5 minutes to release ITF-ITFR binding complex. Proteins were separated by SDS-PAGE and transferred to a Western blotting membrane.

The membrane for Western blotting was incubated in PBS with 0.5% Tween-20, washed three times, and then blocked for 2 to 3 hours with 1% BSA. The membrane was then incubated overnight with first antibody (anti-thioredoxin) in 1% BSA overnight. After washing three times, the membrane was incubated with the second antibody (anti-mouse IgG) at room temperature for 1 hour. Finally, the membrane was washed five times and cross-linked receptor was identified by chemiluminescence.

This analysis revealed that rat or human ITFR has a molecular weight of about 50–60 kD or 75–80 kD. A 96.4 kD band and a 66 kD band were identified as specifically associate with ITF-TRX. These molecular weights correspond to the molecular weight of a binding complex of ITF-TXR and ITFR. Thus, ITFR is predicted to be a 50–60 kD protein or a 75–80 kD protein.

The ITFR identified by the present invention can be used to generate anti-ITFR antibodies by any means known in the art. For example, ITFR can be separated from ITF-ITFR binding complexes by boiling the ITF-ITFR binding complexes and running the boiled sample on a denatured SDS-PAGE gel. A band of the molecular weight representing ITFR can be cut out from the SDS-PAGE gel and used as an immunogen to generate anti-ITFR antibodies. The ITFR gel slice can also be used for ITFR purification. The purified ITFR can be microsequenced. Amino acid sequences obtained from the microsequencing can be used to make degenerated oligonucleotides which are useful for obtaining ITFR cDNA and ITFR genomic sequences.

Screening Assays Employing Intestinal Trefoil Protein Receptor

The ITF receptor can be used in screening assays to identify molecules which bind to ITF receptor. Such molecules may act as receptor agonists or antagonists. In particular, the ITF receptor can be used to identify receptor-binding fragments and analogs of ITF.

The following assays are designed to identify compounds that interact with ITFR and compounds which alter the expression of ITFR.

The compounds which may be screened in accordance with the invention include, but are not limited to peptides, antibodies and fragments thereof, and other organic compounds (e.g., peptidomimetics) that bind to ITFR and either mimic the activity triggered by the natural ligand (i.e., agonists) or inhibit the activity triggered by the natural ligand (i.e., antagonists). The compounds also include peptides and antibodies (or fragments thereof) that resemble ITF (or a portion thereof) and bind to ITFR.

Such compounds may include, but are not limited to, peptides such as, for example, soluble peptides, including but not limited to members of random peptide libraries; (see, e.g., Lam et al., Nature 354:82–84, 1991; Houghten et al., Nature 354:84–86, 1991), and combinatorial chemistry-derived molecular library made of D- and/or L- configuration amino acids, phosphopeptides (including, but not limited to, members of random or partially degenerate, directed phosphopeptide libraries; see, e.g., Songyang et al., Cell 72:767–778, 1993), antibodies (including, but not limited to, polyclonal, monoclonal, humanized, anti-idiotypic, chimeric or single chain antibodies, and FAb, F(ab')$_2$ and FAb expression library fragments, and epitope-binding fragments thereof), and small organic or inorganic molecules.

In vitro systems can be used to identify compounds capable of binding ITFR. A test compound can be incubated with cells expressing ITFR, e.g., IEC-6 cells, LS174 cells, and HT-29 cells under a condition and for a sufficient period of time which allows complex formation between ITF and the test compound. The complex of ITFR and the test compound can be detected in the reaction mixture by competition with the binding of ITF or an ITF fusion protein to ITFR.

The screening assays can be conducted in a variety of ways. For example, one method to conduct such an assay involves anchoring the ITFR-expressing cells onto a solid phase and detecting ITFR/test compound complexes anchored on the solid phase at the end of the reaction. In one embodiment of such a method, ITFR-expressing cells may be anchored onto a solid surface, and the test compound, which is not anchored, may be labeled, either directly or indirectly.

In practice, microtiter plates may conveniently be utilized as the solid phase. The anchored component may be immobilized by non-covalent or covalent attachments. For example, an immobilized antibody, preferably a monoclonal antibody, specific for the cells or protein to be immobilized may be used to anchor the cells or protein to the solid surface. The surfaces may be prepared in advance and stored.

In order to conduct the assay, the non-immobilized component is added to the coated surface containing the anchored component. After the reaction is completed, unreacted components are removed (e.g., by washing) under conditions such that any complexes formed will remain immobilized on the solid surface. The detection of complexes anchored on the solid surface can be accomplished in a number of ways. Where the previously non-immobilized component is pre-labeled, the detection of label immobilized on the surface indicates that complexes were formed. Where the previously non-immobilized component is not pre-labeled, an indirect label can be used to detect complexes anchored on the surface, e.g., using a labeled antibody specific for the previously non-immobilized component (the antibody, in turn, may be directly labeled or indirectly labeled with a labeled anti-Ig antibody) or by competition for detectable ITF, e.g., the ITF fusion protein described below.

Alternatively, a reaction can be conducted in a liquid phase where the reaction products can be separated from unreacted components and the binding complexes can be detected. For example, an immobilized antibody specific for ITFR-expressing cells or the test compound can be used to anchor any possible complexes formed in the solution. Subsequently, these anchored complexes can be identified by a labeled antibody specific for the complex-component that is free from the direct interaction with the immobilized antibody.

Any of the above described assays can be carried out using solubilized or purified ITFR.

Compounds which bind to ITFR can be tested for their ability to protect the digestive tract against damage using the dextran suflate sodium (DSS) murine model system. In this model system mice are administered for seven days with DSS (2.5% w/v) either with or without a treatment. A colon transection is fixed in 4% paraformaldehyde, mounted in paraffin, and stained with hematoxylin and eosin. Obvious ulceration and hemorrhage are signs of damage.

The DSS model described above provides a system for testing the protective effects of ITF, active polypeptide fragments or variants thereof, or compounds which bind ITFR and/or enhance ITFR activity. One can administer a compound to be tested to DSS-treated mice, either wild type or ITF-deficient mice, and determine whether the compound has therapeutic effects by performing the assays described above.

In addition to the use of DSS, any chemical compound that is known to damage the mucosa lining the digestive tract can be used to establish a system for assaying the protective effect of ITF, ITFR, and the variants thereof. These compounds include, but are not limited to, alcohol, indomethacin, and methotrexate.

For example, methotrexate (MTX) can be administered intraperitoneally to mice at a dose of 40 mg/kg. One group of MTX-treated animals could be given, in addition, the protein to be tested for protective effect. Various parameters, such as body weight, the presence of lesions in the digestive tract, and mortality of these animals could then be compared to equivalent measurements taken from animals that were not treated with the protein.

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawing.

I claim:

1. A substantially pure human intestinal trefoil factor receptor (ITFR), characterized in that it specifically binds to human ITF, has a molecular weight of about 75–80 kD when analyzed by SDS-PAGE, and is expressed by human intestinal or human colonic cells.

2. The ITFR of claim 1, wherein said ITFR is expressed by human intestinal epithelial cells or human colonic epithelial cells.

* * * * *

UNITED STATES PATENT AND TRADEMARK OFFICE
CERTIFICATE OF CORRECTION

PATENT NO. : 6,426,404 B1
DATED : July 30, 2002
INVENTOR(S) : Daniel K. Podolsky It is certified that error appears in the above-identified patent and that said Letters Patent is hereby corrected as shown below:

Column 4,
Line 2, change "antibody,." to -- antibody, --
Line 14, change "MRNA" to -- mRNA --

Signed and Sealed this

Twenty-ninth Day of June, 2004

JON W. DUDAS
*Acting Director of the United States Patent and Trademark Office*